United States Patent
Nestler

(10) Patent No.: US 6,207,809 B1
(45) Date of Patent: Mar. 27, 2001

(54) PROCESS FOR THE PREPARATION OF AQUEOUS DIAZONIUM SALT SOLUTIONS

(75) Inventor: Bernd Nestler, Frankfurt am Main (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/564,374

(22) Filed: May 2, 2000

(30) Foreign Application Priority Data

May 8, 1999 (DE) ............................................. 199 21 498

(51) Int. Cl.$^7$ .................................................. C07C 245/20
(52) U.S. Cl. .................................................................. 534/565
(58) Field of Search ............................................... 534/565

(56) References Cited

U.S. PATENT DOCUMENTS 4,845,288 * 7/1989 Lantzsch et al. ................ 534/565 X
5,051,131 9/1991 Yuasa et al. ......................... 106/494

FOREIGN PATENT DOCUMENTS 43 16 923    11/1994   (DE) .
1 431 815    2/1966    (FR) .

OTHER PUBLICATIONS

Beller et al., Chemical Abstracts, 122:80859, 1995.*
Beller et al., Chemical Abstracts, 122:9653, 1995.*
EPO search report.
Derwent Patent Family Abstract FR 1 431 815.
Derwent Patent Family Abstract for DE 43 16 923.

* cited by examiner

Primary Examiner—Fiona T. Powers
(74) Attorney, Agent, or Firm—Scott E. Hanf

(57) ABSTRACT

An aqueous solution of diazonium salts is prepared in the absence of organic solvents by reducing a water-soluble aromatic nitro compound in aqueous solution with hydrogen and a hydrogenation catalyst to give the aromatic amino compound, and diazotizing this amino compound in the aqueous solution.

11 Claims, No Drawings

PROCESS FOR THE PREPARATION OF AQUEOUS DIAZONIUM SALT SOLUTIONS

BACKGROUND OF THE INVENTION

This invention relates to a novel process for the preparation of aqueous diazonium salt solutions. Aqueous diazonium salt solutions are used, for example, for the preparation of azo compounds, in particular of dyes and pigments. In the literature only a few methods for the preparation of aqueous diazonium salt solutions, starting from aromatic nitro compounds, are described, and even these have only been developed for the synthesis of small amounts for scientific purposes.

Usually, the aromatic nitro compound is firstly reduced to give the corresponding aromatic amine which, following work-up and isolation, is reacted in a second, separate step with an alkaline earth metal nitrite to give the desired diazonium salt. Here, the reduction is usually carried out as a catalytic hydrogenation using a suitable catalyst. The solvents normally used are organic solvents, in particular low molecular weight alcohols, such as methanol, ethanol or propanol, and also corresponding esters, such as, for example, ethyl acetate. After the aromatic amine formed in the process has been isolated, it is reacted in aqueous solution with nitrite to give the corresponding diazonium salt.

A procedure of this type is described in U.S. Pat. No. 5,051,131. Here, aromatic nitro compounds prepared by reacting nitrobenzoyl chloride derivatives and nitrobenzenesulfonyl chloride derivatives with aliphatic bisamines are reduced in ethanolic solution using a palladium catalyst to give the corresponding aromatic amine, and the latter is isolated from the solution. In the next step, the isolated amine is reacted in aqueous acetic acid solution with sodium nitrite to give the desired diazonium salt solution. A disadvantage of this procedure is the use of different solvents in the two reaction stages since, following the first stage, the organic solvent used has to be removed in a separate step and is formed as a waste product.

Because of the combustibility and possible formation of ignitable solvent vapor/air mixtures, this step is complex on an industrial scale and is also unacceptable from a safety viewpoint.

SUMMARY OF THE INVENTION

The object of this invention is to find a simple process for the preparation of aqueous solutions of diazonium salts of the formula (1), starting from aromatic nitro compounds of the formula (2). In addition, the process according to the invention should avoid solvents which are unacceptable in terms of safety, and the resulting products should be produced in high yield with minimum amounts of waste.

Surprisingly, we have found that if the aromatic nitro compound of the formula (2) is converted into a water-soluble salt or is in the form of such, it can be reduced in aqueous solution to a salt of the aqueous aromatic amine of the formula (3) which, optionally following removal of the catalyst, can be converted directly using a diazotization reagent, such as, for example, a nitrite, into the desired aqueous diazonium salt solution, without the need to change the solvent.

DESCRIPTION OF THE PREFERRED EMBODIMENTS

The invention provides a process for the preparation of aqueous solutions of diazonium salts of the formula (1)

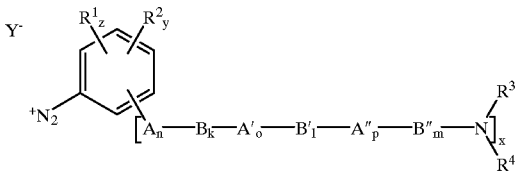

(1)

in which some or all of the amino groups are in protonated form, $R^1$, $R^2$, $R^3$ and $R^4$, independently of one another, are hydrogen, a $C_1$–$C_{16}$-alkyl, $C_3$–$C_7$-cycloalkyl, $C_2$–$C_{16}$-alkenyl, aryl or a 5- to 6-membered aliphatic or aromatic heterocycle, which are optionally substituted by one or more, for example 1, 2, or 3, $C_1$–$C_4$ alkyl radicals, halogen atoms or groups of the formula =O, —OR', —NR'R", —SR', —COR', —COOR', —CONR'R", —NR'CONR"R'" or —SO$_2$NR'R", where R', R", R'" are hydrogen or a $C_1$–$C_{10}$-alkyl, $C_3$–$C_7$-cycloalkyl, $C_2$–$C_{16}$-alkenyl, aryl or a 5- to 6-membered aliphatic or aromatic heterocycle, or where R' and R", or R" and R'", or $R^3$ and $R^4$ together with the adjacent N atom form a 5- or 6-membered aliphatic or aromatic heterocycle, and $R_1$ and $R^2$ can additionally be halogen or groups of the formula —OR', —NR'R"R'", —SR', —COR', —COOR', —CONR'R", —SO$_3$H, —PO$_4$H$_2$, —NR'CONR"R'" or —SO$_2$NR'R";

A, A' and A", independently of one another, are a divalent group of the formula —O—, —NR'—, —S—, —CO—, —COO—, —CONR'—, —NR'CONR"— or —SO$_2$NR'—;

B, B' and B", independently of one another, are a substituted or unsubstituted $C_1$–$C_{14}$-alkylene, $C_3$–$C_7$-cycloalkylene, $C_2$–$C_{14}$-alkenylene, arylene or heteroarylene radical, or B, B' or B" form, together with $R^3$ and/or $R^4$ and the adjacent N atom a 5- to 7-membered heterocycle;

Y⁻ is F⁻, Cl⁻, Br⁻, HSO$_4^-$, ½SO$_4^{2-}$, H$_2$PO$_4^-$, ½HPO$_4^{2-}$, ⅓PO$_4^{3-}$, an anion of a pyro-, meta- or poly-phosphoric acid, BF$_4^-$, PF$_6^-$, HCO$_3^-$, ½CO$_3^{2-}$, NO$_2^-$, NO$_3^-$, formate, acetate, propionate, R""SO$_4^-$, R""SO$_3^-$ or R""COO⁻, where R"" is a substituted or unsubstituted $C_1$–$C_{21}$-alkyl or aryl radical, preferably $C_1$–$C_{10}$-alkyl, naphthyl or phenyl;

k, l and m, independently of one another, are the number 0, 1, 2 or 3;

n, o and p, independently of one another, are the numbers 0 or 1;

x is an integer from 1 to 3; and y and z are each an integer from 1 to 4, where the sum x+y+z is 3 to 5, which comprises reacting an aqueous solution of a water-soluble salt of the aromatic nitro compound of the formula (2),

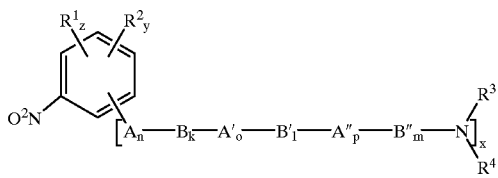

(2)

with hydrogen and in the presence of a catalyst which catalyzes the reduction of aromatic nitro groups to amino groups, and diazotizing the aromatic amine formed in the process in the aqueous solution with a diazotization reagent to give the diazonium salt.

In the above definitions, aryl is preferably phenyl or naphthyl. Preference is given to compounds of the formula (1) and (2) in which A, A' and A" are —O—, —NR'—, —CONR' or —SO$_2$NR'—.

Also preferred are compounds of the formula (1) and (2) in which B, B' and B" are C$_2$–C$_6$-alkylene, C$_6$–C$_{10}$-arylene, benzylene or pyridylene which are unsubstituted or substituted by 1 to 4 radicals from the group consisting of C$_1$–C$_4$-alkyl, C$_1$–C$_4$-alkoxy, OH, NH$_2$, NH(C$_1$–C$_4$-alkyl), NH(C$_1$–C$_4$-alkyl)$_2$, COOH, CONH$_2$, CONH(C$_1$–C$_4$-alkyl), CON(C$_1$–C$_4$-alkyl)$_2$, F and Cl, or together with R$^3$ and/or R$^4$ form a heterocycle from the group consisting of pyrrolidine, piperidine, piperazine and morpholine which is optionally substituted by 1 to 6 radicals from the group consisting of C$_1$–C$_4$-alkyl, C$_1$–C$_4$-alkoxy, OH, NH$_2$, NH(C$_1$–C$_4$-alkyl), NH(C$_1$–C$_4$-alkyl)$_2$, COOH, CONH$_2$, CONH(C$_1$–C$_4$-alkyl), CON(C$_1$–C$_4$-alkyl)$_2$, F and Cl.

Also preferred are compounds of the formula (1) and (2) in which R$^1$ and R$^2$ are C$_1$–C$_6$-alkyl, C$_5$–C$_6$-cycloalkyl, C$_2$–C$_6$-alkenyl, C$_6$–C$_{10}$-aryl or pyridinyl which are optionally substituted by 1 to 3 radicals from the group consisting of fluorine, bromine, C$_1$–C$_4$-alkoxy, NH$_2$, N(C$_1$–C$_4$-alkyl)$_2$, NH(C$_1$–C$_4$-alkyl), COH, CO(C$_1$–C$_4$-alkyl), COOH, —COO(C$_1$–C$_4$-alkyl), CONH$_2$, CONH(C$_1$–C$_4$-alkyl), CON(C$_1$–C$_4$-alkyl)$_2$, SO$_2$NH$_2$, SO$_2$NH(C$_1$–C$_4$-alkyl), SO$_2$N(C$_1$–C$_4$-alkyl)$_2$ and SO$_3$H; or hydrogen, fluorine, chlorine, bromine, C$_1$–C$_4$-alkoxy, NH$_2$, NH(C$_1$–C$_4$-alkyl), N(C$_1$–C$_4$-alkyl)$_2$, S(C$_1$–C$_4$-alkyl), CO(C$_1$–C$_4$-alkyl), COOH, COO(C$_1$–C$_4$-alkyl), CONH$_2$, CONH(C$_1$–C$_4$-alkyl), CON(C$_1$–C$_4$-alkyl)$_2$, SO$_3$H, SO$_2$NH$_2$, SO$_2$NH(C$_1$–C$_4$-alkyl) or SO$_2$N(C$_1$–C$_4$-alkyl)$_2$.

Also preferred are compounds of the formula (1) and (2) in which R$^3$ and R$^4$ are C$_1$–C$_6$-alkyl, C$_5$–C$_6$-cycloalkyl, C$_2$–C$_6$-alkenyl, C$_6$–C$_{10}$-aryl or pyridinyl which are optionally substituted by 1 to 3 radicals from the group consisting of fluorine, chlorine, bromine, C$_1$–C$_4$-alkoxy, NH$_2$, N(C$_1$–C$_4$-alkyl)$_2$, NH(C$_1$–C$_4$-alkyl), COH, CO(C$_1$–C$_4$-alkyl), COOH, —COO(C$_1$–C$_4$-alkyl), CONH$_2$, CONH(C$_1$–C$_4$-alkyl), CON(C$_1$–C$_4$-alkyl)$_2$, SO$_2$NH$_2$, SO$_2$NH(C$_1$–C$_4$-alkyl), SO$_2$N(C$_1$–C$_4$-alkyl)$_2$ and SO$_3$H; or hydrogen.

Also preferred are compounds of the formula (1) and (2) in which m and p are zero.

Also preferred are compounds of the formula (1) and (2) in which x is the number 1 or 2.

Also preferred are compounds of the formula (1) in which Y$^-$ is Cl$^-$, HSO$_4^-$, ½SO$_4^{2-}$, H$_2$PO$_4^-$, ½HPO$_4^{2-}$, ⅓PO$_4^{3-}$, an anion of pyro-, meta- or poly-phosphoric acid, acetate or propionate.

The aromatic nitro compounds of the formula (2) used according to the invention also include salts derived therefrom in which the amino group(s) is/are in protonated form and one or more counterions, such as, for example, F$^-$, Cl$^-$, Br$^-$, HSO$_4^-$, SO$_4^{2-}$, H$_2$PO$_4^-$, HPO$_4^{2-}$, PO$_4^{3-}$, anions of pyro-, meta- or poly-phosphoric acid, BF$_4^-$, PF$_6^-$, HCO$_3^-$, CO$_3^{2-}$, NO$_2^-$, NO$_3^-$, formate, acetate or propionate, and anions of the type R""SO$_4^-$, R""SO$_3^-$, R""COO$^-$, where R"" is as defined above, are present. Preference is given here to F$^-$, Cl$^-$, HSO$_4^-$, SO$_4^{2-}$, H$_2$PO$_4^-$, HPO$_4^{2-}$, PO$_4^{3-}$, NO$_3^-$, acetate or propionate ions.

The aromatic nitro compounds used are preferably compounds which can be converted into a water-soluble salt and as such are stable to hydrolysis. Examples of compounds of this type are:

ortho-, meta- and para-N,N-dimethylnitroaniline,
ortho-, meta- and para-N,N-diethylnitroaniline,
ortho-, meta- and para-N,N-dipropylnitroaniline,
ortho-, meta- and para-N-(2-dimethylaminoethyl)nitrobenzamide,
ortho-, meta- and para-N-(2-diethylaminoethyl)nitrobenzamide,
ortho-, meta- and para-N-(2-dipropylaminoethyl)nitrobenzamide,
ortho-, meta- and para-N-(2-dibutylaminoethyl)nitrobenzamide,
ortho-, meta- and para-N-(3-dimethylaminopropyl)nitrobenzamide,
ortho-, meta- and para-N-(3-diethylaminopropyl)nitrobenzamide,
ortho-, meta- and para-N-(3-dipropylaminopropyl)nitrobenzamide,
ortho-, meta- and para-N-(3-dibutylaminopropyl)nitrobenzamide,
ortho-, meta- and para-N-(piperidin-4-yl)nitrobenzamide,
ortho-, meta- and para-N-(2,2,6,6-tetramethylpiperidin-4-yl)nitrobenzamide,
N-(2,2,6,6-tetramethylpiperidin-4-yl)-3-nitrobenzamide,
N-(2,2,6,6-tetramethylpiperidin-4-yl)-4-methyl-3-nitrobenzamide,
4-methyl-1-(4-nitrobenzoyl)piperazine,
N-(2-morpholin-4-ylethyl)-4-nitrobenzamide,
N-(2-imidazol-1-ylethyl)-4-nitrobenzamide,
1-(2-nitrobenzoyl)-4,7,7-trimethyldiethylenetriamine,
1-(3-nitrobenzoyl)-4,7,7-trimethyldiethylenetriamine,
1-(4-nitrobenzoyl)-4,7,7-trimethyldiethylenetriamine,
1-(4-nitrobenzoyl)-4,7,7-triethyldiethylenetriamine,
ortho-, meta- and para-N-(2-dimethylaminoethyl)nitrobenzenesulfonamide,
ortho-, meta- and para-N-(2-diethylaminoethyl)nitrobenzenesulfonamide,
ortho-, meta- and para-N-(2-dipropylaminoethyl)nitrobenzenesulfonamide,
ortho-, meta- and para-N-(2-dibutylaminoethyl)nitrobenzenesulfonamide,
ortho-, meta- and para-N-(3-dimethylaminopropyl)nitrobenzenesulfonamide,
ortho-, meta- and para-N-(3-diethylaminopropyl)nitrobenzenesulfonamide,
ortho-, meta- and para-N-(3-dipropylaminopropyl)nitrobenzenesulfonamide,
ortho-, meta- and para-N-(3-dibutylaminopropyl)nitrobenzenesulfonamide, N-2-dimethylaminoethyl-N'-(4-nitrophenyl)urea,
N-2-diethylaminoethyl-N'-(4-nitrophenyl)urea,
N-2-diethylaminoethyl-N'-(3-nitrophenyl)urea,
N-3-dimethylaminopropyl-N'-(4-nitrophenyl)urea,
N-3-diethylaminopropyl-N'-(4-nitrophenyl)urea,
dimethyl-2-(2-nitrophenoxy)ethylamine,
diethyl-2-(2-nitrophenoxy)ethylamine,
dipropyl-2-(2-nitrophenoxy)ethylamine,
dimethyl-3-(3-nitrophenoxy)propylamine,
diethyl-3-(3-nitrophenoxy)propylamine,
dipropyl-3-(3-nitrophenoxy)propylamine,
1-methyl-4-(4-nitrophenoxy)piperidine,
1-ethyl-4-(3-nitrophenoxy)piperidine,
3-(4-nitrophenoxy)propylmorpholine,
4-dimethylamino-1-(4-nitrophenyl)butan-1-one,
4-nitrophenyl-4-oxo-butylpiperidine,
2-dimethylaminoethyl ortho-, meta- and para-nitrobenzoate,
2-diethylaminoethyl ortho-, meta- and para-nitrobenzoate,
3-dimethylaminopropyl ortho-, meta- and para-nitrobenzoate,
3-diethylaminopropyl ortho-, meta- and para-nitrobenzoate,
N,N,N'-trimethyl-N'-nitrophenylphenylenediamine,
N,N-diethyl-N'-methyl-N'-nitrophenylphenylenediamine,
nitro-N,N,N',N'-tetramethylcarbamoylmethylisophthalamide.

For the process according to the invention, it is insignificant by which route the aqueous solution of the water-soluble salt of the aromatic nitro compound of the formula (2) is prepared. This solution is advantageously prepared by dissolving the corresponding salt in water, or by reacting the aromatic nitro compound with acid to give the corresponding salt. In the process, it is insignificant whether the nitro compound is added to the acid or the acid is added to the nitro compound. This reaction is advantageously carried out in aqueous solution, although it is also possible to carry it out in organic or multiphase solvent systems, i.e. mixtures of water and organic solvents, and to separate off the desired water-soluble salt of the aromatic nitro compound of the formula (2), e.g. by extraction.

The concentration of the salt of the aromatic nitro compound of the formula (2) in the aqueous solution can be 0.001 to 25, preferably 0.05 to 15, particularly preferably 0.1 to 5, mol per liter of solution.

The reaction of the aqueous solution of the water-soluble salt of the aromatic nitro compound of the formula (2) takes place by heterogeneous hydrogenation with $H_2$ and in the presence of a suitable catalyst. Suitable catalysts are those which catalyze the reduction of a nitro group with hydrogen to give an amino group. Examples of such reductions and suitable catalysts are given, for example, in R. Schröter "Amine" Methoden der Organischen Chemie ["Amines" Methods in Organic Chemistry], Houben-Weyl, E. Müller (Ed.), vol. XI/1 (1957), pp. 360–488. Preferred catalysts are hydrogenation catalysts derived from transition metals, in particular from noble metals, such as, for example, Raney nickel, cobalt, iridium, palladium, platinum, rhenium, rhodium, ruthenium, osmium, zinc, alloys of these metals, oxides of these metals, such as, for example, PdO, $PtO_2$, $Rh_2O_3$, $RuO_2$, ZnO; and also catalysts in which these metals, alloys or oxides are applied to suitable support materials, such as carbon, activated carbon, aluminum oxide, activated aluminum oxide, silicates, and Ca, Sr and Ba carbonate and sulfate. The concentration of the catalyst is usually in the range from 0.0001 to 25% by weight, preferably from 0.001 to 20% by weight, particularly preferably from 0.005 to 15% by weight, based on the weight of the compound of the formula (2).

In the reaction with hydrogen, the concentration of the compound of the formula (2) is advantageously in the range from 0.001 to 25 mol per liter of solution, preferably 0.05 to 15 mol/l, particularly preferably 0.1 to 5 mol/l. The reaction with hydrogen can be carried out under atmospheric pressure. In order to accelerate the reaction, it can also be carried out under an increased $H_2$ pressure, e.g. of from 1 to 200 bar, preferably from 2 to 150 bar, in particular from 5 to 100 bar.

The reaction is advantageously carried out at temperatures between 0 and 250° C., preferably at 10 to 140° C. The period of time required for this is from about 5 minutes to 3 days, depending on pressure, temperature, catalyst and concentration ratios.

When the reaction with hydrogen is complete, the catalyst is advantageously separated off, e.g. by filtration, in order to permit reuse, although it is also possible to leave it in the reaction solution.

The aqueous solution resulting from the reaction with hydrogen is, optionally after concentration or dilution, admixed with a diazotization reagent. An overview of the suitable diazotization reagents and appropriate processes for their reaction is given, for example, in R. Pütter "Stickstoff-Verbindungen I" Methoden der Organischen Chemie ["Nitrogen compounds I" Methods in Organic Chemistry], Houben-Weyl, R. Stroh (Ed.), vol. X/3 (1965), pp. 1–66 and A. Engel "Organo-Stickstoff-Verbindungen I" Methoden der Organischen Chemie ["Organonitrogen compounds I" Methods in Organic Chemistry], Houben-Weyl, D. Klamann (Ed.), vol. E 16a (1990), pp. 1060–1079 and the literature cited therein.

Although it is unimportant for the process according to the invention which diazotization reagents are used, advantageous reagents are, however, those which can be used in aqueous solution. Examples of diazotization reagents of this type are alkali metal and alkaline earth metal nitrites, nitrosylsulfuric acid, nitrous gases or organic nitrites. Preference is given in this connection to alkali metal nitrites, nitrosylsulfuric acid and nitrous gases, and particular preference is given to sodium nitrite and nitrosylsulfuric acid, and aqueous solutions thereof.

The concentration of the amino compound to be diazotized is advantageously in the range from 0.001 to 25 mol per liter of solution, preferably from 0.05 to 15 mol/l, particularly preferably from 0.1 to 5 mol/l.

The diazotization reagents can be used in stoichiometric amount, although it can also be advantageous to use them in deficit or excess.

Preference is given to the use of from 0.8 to 2 equivalents, particularly preferably from 0.95 to 1.3 equivalents, of diazotization reagent.

Because of the thermal lability of diazonium salts, the reaction with the diazotization reagent is generally carried out in the temperature range from −15° C. to +30° C., preferably in the range from −5° C. to +15° C. Here, cooling can particularly advantageously be effected by adding ice, although, alternatively or additionally, the cooling can also be indirect, i.e. by using heat exchangers.

Since, inter alia, the rate of the reaction with diazotization reagents and the stability of diazonium salts are dependent on the pH, it may prove advantageous to adjust the pH to a suitable value by adding acid, base or buffer before, during and/or after the reaction with the diazotization reagent. Suitable agents for this purpose are, in particular, mineral acids, low molecular weight organic acids, alkali metal hydroxides, phosphate and acetate buffers; preference is given to hydrochloric acid, sulfuric acid, phosphoric acid, acetic acid, sodium hydroxide solution, potassium hydroxide solution, mixtures of these acids or alkalis, and to buffer mixtures derived therefrom. Preference is given to a pH of from 0 to 9, in particular a pH of from 0.5 to 6.

When the diazotization reaction is complete, the resulting aqueous diazonium salt solution of the formula (1) can be directly reused. However, it is also possible to remove any excess of diazotization reagent which may be present in the reaction solution using suitable reagents, such as, for example, amidosulfonic acid. It may also be advantageous to remove by filtration any insoluble impurities which may be present.

The process according to the invention is notable for the fact that it avoids organic solvents, meaning that a step for their removal is not necessary and that they are not produced as waste material. In addition, very good yields are achieved.

EXAMPLES

In the examples below the percentages are percentages by weight.

Example 1

Synthesis of aqueous 4-(3-diethylaminopropyl) carbamoyl-benzenediazonium Chloride Solution in Methanolic Solution (comparative example)

315 g of N-(3-diethylaminopropyl)-4-nitrobenzamide hydrochloride (998 mmol) were dissolved in 2.8 l of methanol, 28 g of palladium catalyst (5% palladium on activated carbon, 55% water content) were added, and the mixture was stirred for 3 h at a pressure of 50 bar under a hydrogen atmosphere. The catalyst was filtered off, and the solvent was dissolved off from the resulting solution. 310 g of a viscous oil were obtained. 93.3 g of this oil (about 0.3 mol) were dissolved in 300 ml of water and 93 ml of hydrochloric acid (31%) and cooled to 0° C. with ice, and, over the course of 5 minutes, 36 ml of sodium nitrite solution (40%) (251 mmol) were added thereto. The mixture was then stirred for 30 minutes, then the nitrite excess was removed by adding amidosulfonic acid (negative nitrite test with diphenyl sulfone). 800 ml of 8.2% strength by weight diazonium salt solution were obtained. Yield 84%.

Example 2

Synthesis of Aqueous 4-(3-diethylaminopropyl) carbamoyl-benzenediazonium Chloride Solution in Aqueous Solution 6.00 g of palladium catalyst (5% palladium on activated carbon, 57% water content) were added to a solution of 63.2 g of N-(3-diethylaminopropyl)-4-nitrobenzamide hydrochloride (200 mmol) in 500 ml of water, and the mixture was stirred under a hydrogen atmosphere at a pressure of 50 bar until the hydrogen uptake was complete (duration about 0.5 h). The catalyst was filtered off, 62 ml of hydrochloric acid (31%) were added to the resulting solution, which was cooled to 0° C. with ice and, over the course of 5 min, diazotized with 25.0 ml of sodium nitrite solution (40%) (189 mmol). After the mixture had been stirred for 30 min, the nitrite excess was removed by adding amidosulfonic acid (negative nitrite test with diphenyl sulfone). 850 ml of 5.8% strength by weight diazonium salt solution were obtained.

Yield 95%.

Aqueous solutions of the following diazonium salts were prepared in a manner analogous to that in Example 2:

Example 3

3-(2-dimethylaminoethyl) carbamoylbenzenediazonium Chloride yield: 93%

Example 4

4-[2-(2-dimethylaminoethyl)methylaminoethyl] carbamoylbenzene-diazonium Chloride yield: 94%

Example 5

4-(3-diethylaminopropyl) sulfamoylbenzenediazonium chloride yield: 95%

What is claimed is:
1. A process for the preparation of aqueous solutions of diazonium salts of the formula (1)

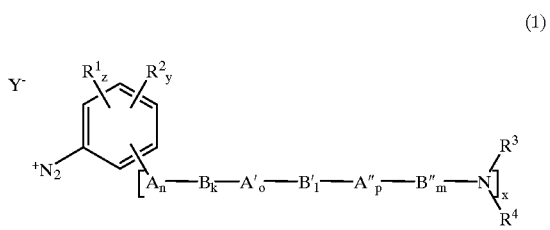

in which some or all of the amino groups are in protonated form, $R^1$, $R^2$, $R^3$ and $R^4$, independently of one another, are hydrogen, a $C_1$–$C_{16}$-alkyl, $C_3$–$C_7$-cycloalkyl, $C_2$–$C_{16}$-alkenyl, aryl or a 5- to 6-membered aliphatic or aromatic heterocycle, which are optionally substituted by one or more $C_1$–$C_4$ alkyl radicals, halogen atoms or groups of the formula =O, —OR', —NR'R", —SR', —COR', —COOR', —CONR'R", —NR'CONR"R'" or —SO$_2$NR'R", where R', R", R'" are hydrogen or a $C_1$–$C_{10}$-alkyl, $C_3$–$C_7$-cycloalkyl, $C_2$–$C_{16}$-alkenyl, aryl or a 5- to 6-membered aliphatic or aromatic heterocycle, or where R' and R", or R" and R'", or $R^3$ and $R^4$ together with the adjacent N atom form a 5- or 6-membered aliphatic or aromatic heterocycle, and $R^1$ and $R^2$ may additionally be halogen or groups of the formula —OR', —NR'R"R'", —SR', —COR', —COOR', —CONR'R", —SO$_3$H$_2$, —PO$_4$H$_2$, —NR'CONR"R'" or —SO$_2$NR'R";

A, A' and A", independently of one another, are a divalent group of the formula —O—, —NR'—, —S—, —CO—, —COO—, —CONR'—, —NR'CONR"— or —SO$_2$NR'—;

B, B' and B", independently of one another, are a substituted or unsubstituted $C_1$–$C_{14}$-alkylene, $C_3$–$C_7$-cycloalkylene, $C_2$–$C_{14}$-alkenylene, arylene or heteroarylene radical, or B, B' or B" form, together with $R^3$ and/or $R^4$ and the adjacent N atom a 5- to 7-membered heterocycle;

$Y^-$ is $F^-$, $Cl^-$, $Br^-$, $HSO_4^-$, $\frac{1}{2}SO_4^{2-}$, $H_2PO_4^-$, $\frac{1}{2}HPO_4^{2-}$, $\frac{1}{3}PO_4^{3-}$, an anion of a pyro-, meta- or poly-phosphoric acid, $BF_4^-$, $PF_6^-$, $HCO_3^-$, $\frac{1}{2}CO_3^{2-}$, $NO_2^-$, $NO_3^-$, formate, acetate, propionate, $R''''SO_4^-$, $R''''SO_3^-$ or $R''''COO^-$, where $R''''$ is a substituted or unsubstituted $C_1$–$C_{21}$-alkyl or aryl radical;

k, l and m, independently of one another, are the number 0, 1, 2 or 3;

n, o and p, independently of one another, are the numbers 0 or 1;

x is an integer from 1 to 3; and y and z are each an integer from 1 to 4, where the sum x+y+z is 3 to 5, which comprises reacting an aqueous solution of a water-soluble salt of the aromatic nitro compound of the formula (2),

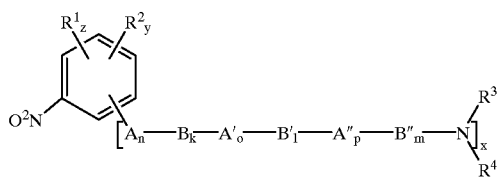

(2)

with hydrogen and in the presence of a catalyst which catalyzes the reduction of aromatic nitro groups to amino groups, and diazotizing the aromatic amine formed in the process in the aqueous solution with a diazotization reagent to give the diazonium salt.

2. The process as claimed in claim 1, wherein A, A' and A" are —O—, —NR'—, —CONR'— or —SO$_2$NR'—.

3. The process as claimed in claim 1, wherein B, B' and B" are $C_2$–$C_6$-alkylene, $C_6$–$C_{10}$-arylene, benzylene or pyridylene which are unsubstituted or substituted by 1 to 4 radicals from the group consisting of $C_1$–$C_4$-alkyl, $C_1$–$C_4$-alkoxy, OH, NH$_2$, NH($C_1$–$C_4$-alkyl), NH($C_1$–$C_4$-alkyl)$_2$, COOH, CONH$_2$, CONH($C_1$–$C_4$-alkyl), CON($C_1$–$C_4$-alkyl)$_2$, F and Cl, or together with $R^3$ and/or $R^4$ form a heterocycle from the group consisting of pyrrolidine, piperidine, piperazine and morpholine which is optionally substituted by 1 to 6 radicals from the group consisting of $C_1$–$C_4$-alkyl, $C_1$–$C_4$-alkoxy, OH, NH$_2$, NH($C_1$–$C_4$-alkyl), NH($C_1$–$C_4$-alkyl)$_2$, COOH, CONH$_2$, CONH($C_1$–$C_4$-alkyl), CON($C_1$–$C_4$-alkyl)$_2$, F and Cl.

4. The process as claimed in claim 1, wherein $R^1$ and $R^2$ are $C_1$–$C_6$-alkyl, $C_5$–$C_6$-cycloalkyl, $C_2$–$C_6$-alkenyl, $C_6$–$C_{10}$-aryl or pyridinyl which are optionally substituted by 1 to 3 radicals from the group consisting of fluorine, chlorine, bromine, $C_1$–$C_4$-alkoxy, NH$_2$, N($C_1$–$C_4$-alkyl)$_2$, NH($C_1$–$C_4$-alkyl), COH, CO($C_1$–$C_4$-alkyl), COOH, —COO($C_1$–$C_4$-alkyl), CONH$_2$, CONH($C_1$–$C_4$-alkyl), CON($C_1$–$C_4$-alkyl)$_2$, SO$_2$NH$_2$, SO$_2$NH($C_1$–$C_4$-alkyl), SO$_2$N($C_1$–$C_4$-alkyl)$_2$ and SO$_3$H; or hydrogen, fluorine, chlorine, bromine, $C_1$–$C_4$-alkoxy, NH$_2$, NH($C_1$–$C_4$-alkyl), N($C_1$–$C_4$-alkyl)$_2$, S($C_1$–$C_4$-alkyl), CO($C_1$–$C_4$-alkyl), COOH, COO($C_1$–$C_4$-alkyl), CONH$_2$, CONH($C_1$–$C_4$-alkyl), CON($C_1$–$C_4$-alkyl)$_2$, SO$_3$H, SO$_2$NH$_2$, SO$_2$NH($C_1$–$C_4$-alkyl) or SO$_2$N($C_1$–$C_4$-alkyl)$_2$.

5. The process as claimed in claim 1, wherein $R^3$ and $R^4$ are $C_1$–$C_6$-alkyl, $C_5$–$C_6$-cycloalkyl, $C_2$–$C_6$-alkenyl, $C_6$–$C_{10}$-aryl or pyridinyl which are optionally substituted by 1 to 3 radicals from the group consisting of fluorine, chlorine, bromine, $C_1$–$C_4$-alkoxy, NH$_2$, N($C_1$–$C_4$-alkyl)$_2$, NH($C_1$–$C_4$-alkyl), COH, CO($C_1$–$C_4$-alkyl), COOH, —COO($C_1$–$C_4$-alkyl), CONH$_2$, CONH($C_1$–$C_4$-alkyl), CON($C_1$–$C_4$-alkyl)$_2$, SO$_2$NH$_2$, SO$_2$NH($C_1$–$C_4$-alkyl), SO$_2$N($C_1$–$C_4$-alkyl)$_2$ and SO$_3$H; or hydrogen.

6. The process as claimed in claim 1, wherein m and p are zero.

7. The process as claimed in claim 1, wherein x is the number 1 or 2.

8. The process as claimed in claim 1, wherein the concentration of the compound of the formula (2) in the reaction with hydrogen is 0.001 to 25 mol per liter of solution.

9. The process as claimed in claim 1, wherein the diazotization is carried out at a temperature of from −15° C. to +30° C.

10. The process as claimed in claim 1, wherein the diazotization is carried out at a pH between 0 and 9.

11. The process as claimed in claim 1, wherein the diazotization reagent is sodium nitrite or nitrosylsulfuric acid.

* * * * *